US006595208B1

(12) United States Patent
Coffee et al.

(10) Patent No.: US 6,595,208 B1
(45) Date of Patent: Jul. 22, 2003

(54) DISPENSING DEVICE

(75) Inventors: Ronald Alan Coffee, Haslemere (GB); Alastair Bruce Pirrie, Oxford (GB)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 09/463,264

(22) PCT Filed: Aug. 7, 1998

(86) PCT No.: PCT/GB98/02385

§ 371 (c)(1), (2), (4) Date: Apr. 11, 2000

(87) PCT Pub. No.: WO99/07478

PCT Pub. Date: Feb. 18, 1999

(30) Foreign Application Priority Data

Aug. 8, 1997 (GB) ............................................ 9716888

(51) Int. Cl.$^7$ ........................ A61M 11/00; A61M 15/00

(52) U.S. Cl. ............................ 128/203.12; 128/200.14; 239/690

(58) Field of Search ....................... 128/203.12, 203.23, 128/200.14, 200.23; 239/690

(56) References Cited

U.S. PATENT DOCUMENTS

| | | | | |
|---|---|---|---|---|
| 2,749,125 A | | 1/1956 | Ream | |
| 2,945,443 A | | 7/1960 | Aver et al. | |
| 3,096,762 A | | 7/1963 | Winchell | |
| 3,131,131 A | | 4/1964 | Wehner | |
| 3,232,292 A | | 2/1966 | Scheaefer | |
| 3,456,646 A | | 7/1969 | Phillips et al. | |
| 3,837,573 A | | 9/1974 | Wagner | |
| 3,897,905 A | | 8/1975 | Tadewald | |
| 3,930,061 A | | 12/1975 | Scharfenberger | |
| 3,958,959 A | | 5/1976 | Cohen et al. | |
| 3,994,294 A | * | 11/1976 | Knute | 128/DIG. 12 |
| 4,043,331 A | | 8/1977 | Martin et al. | |
| 4,044,404 A | | 8/1977 | Martin et al. | |
| 4,073,002 A | | 2/1978 | Sickles et al. | |
| 4,150,644 A | | 4/1979 | Masaki et al. | |
| 4,186,886 A | | 2/1980 | Sickles | |
| 4,198,781 A | | 4/1980 | Dykes | |
| 4,203,398 A | | 5/1980 | Maruoka | |
| 4,266,721 A | | 5/1981 | Sickles | |
| 4,306,685 A | * | 12/1981 | Coffee | 239/377 |
| 4,356,528 A | | 10/1982 | Coffee | |
| 4,380,786 A | | 4/1983 | Kelly | |
| 4,401,274 A | * | 8/1983 | Coffee | 239/377 |
| 4,439,980 A | | 4/1984 | Biblarz et al. | |
| 4,467,961 A | | 8/1984 | Coffee et al. | |
| 4,476,515 A | | 10/1984 | Coffee | |
| 4,508,265 A | | 4/1985 | Jido | |
| 4,509,694 A | | 4/1985 | Inculet et al. | |
| 4,549,243 A | | 10/1985 | Owen et al. | |
| 4,565,736 A | | 1/1986 | Stein et al. | |

(List continued on next page.)

FOREIGN PATENT DOCUMENTS

| | | |
|---|---|---|
| DE | 2008769 | 9/1970 |
| DE | 4106564 A1 | 9/1992 |
| EP | 0029301 A1 | 5/1981 |

(List continued on next page.)

*Primary Examiner*—Weilun Lo
*Assistant Examiner*—Mital Patel
(74) *Attorney, Agent, or Firm*—Frost Brown Todd LLC

(57) ABSTRACT

A supply pipe (33) supplies a liquid to a comminution site (40) at which the liquid is subjected to an electric field so as to produce charged comminuted material. An electrical discharge electrode (5) produces ions to at least partially electrically discharge the comminuted material. A further electrode (60) spaced from the comminution site (40) by the electrical discharge electrode (50) electrically attracts ions produced by the electrical discharge electrode (50) away from the comminution site (40) until sufficient space charge is built up to divert the ions towards the charged comminuted material to enable the ions at least partially to discharge the comminuted material.

58 Claims, 10 Drawing Sheets

U.S. PATENT DOCUMENTS

| | | | | | |
|---|---|---|---|---|---|
| 4,634,057 | A | * | 1/1987 | Coffee et al. | 239/302 |
| 4,657,793 | A | | 4/1987 | Fisher | |
| 4,659,012 | A | | 4/1987 | Coffee | |
| 4,671,289 | A | | 6/1987 | Wilp | |
| 4,703,891 | A | | 11/1987 | Jackson et al. | |
| 4,735,364 | A | | 4/1988 | Marchant | |
| 4,748,043 | A | | 5/1988 | Seaver et al. | |
| 4,749,125 | A | | 6/1988 | Escallon et al. | |
| 4,779,515 | A | | 10/1988 | Staub, Jr. | |
| 4,788,016 | A | * | 11/1988 | Colclough et al. | 239/3 |
| 4,801,086 | A | | 1/1989 | Noakes | |
| 4,830,872 | A | | 5/1989 | Grenfell | |
| 4,846,407 | A | | 7/1989 | Coffee et al. | |
| 4,962,885 | A | | 10/1990 | Coffee | |
| 4,979,680 | A | | 12/1990 | Bauch et al. | |
| 5,044,564 | A | | 9/1991 | Sickles | |
| 5,086,972 | A | | 2/1992 | Chang et al. | |
| 5,115,971 | A | | 5/1992 | Greenspan et al. | |
| 5,180,288 | A | | 1/1993 | Richter et al. | |
| 5,222,663 | A | | 6/1993 | Noakes et al. | |
| 5,267,555 | A | | 12/1993 | Pajalich | |
| 5,270,000 | A | * | 12/1993 | Goldner et al. | 180/309 |
| 5,381,789 | A | | 1/1995 | Marquardt | |
| 5,402,945 | A | | 4/1995 | Swanson, Jr. | |
| 5,409,162 | A | | 4/1995 | Sickles | |
| 5,483,953 | A | | 1/1996 | Cooper | |
| 5,655,517 | A | | 8/1997 | Coffee | |
| 5,813,614 | A | * | 9/1998 | Coffee | 239/690 |
| 6,105,571 | A | * | 8/2000 | Coffee | 128/200.14 |

FOREIGN PATENT DOCUMENTS

| | | | | |
|---|---|---|---|---|
| EP | 0120 633 | A2 | | 10/1984 |
| EP | 0234841a | | | 9/1987 |
| EP | 0234842 | | | 9/1987 |
| EP | 0250102 | A | | 12/1987 |
| EP | 02050164 | A3 | | 12/1987 |
| EP | 0523963 | A1 | | 7/1992 |
| EP | 0523962 | A1 | | 1/1993 |
| EP | 523964 | A1 | | 1/1993 |
| GB | 1297993 | | | 11/1972 |
| GB | 2018627 | B | | 10/1979 |
| GB | 1569707 | | | 6/1980 |
| GB | 2018627 | B | | 4/1982 |
| GB | 2 128 900 | A | | 5/1984 |
| GB | 0 102 713 | B1 | | 9/1987 |
| GB | 2 201 873 | A | | 9/1988 |
| SU | 1005939 | A | | 6/1981 |
| WO | WO 91/07232 | | | 5/1991 |
| WO | WO 92/15339 | | | 9/1992 |
| WO | WO 93/00937 | | | 4/1993 |
| WO | WO 9412285 | | | 6/1994 |
| WO | WO94 13266 | | | 6/1994 |
| WO | WO 94 14543 | | | 7/1994 |
| WO | WO 94/19042 | | * | 9/1994 |
| WO | WO 95 26235 | | | 10/1995 |
| WO | WO 9526235 | | | 10/1995 |
| WO | WO 9532807 | | | 12/1995 |
| WO | WO 9907478 | | | 2/1999 |

* cited by examiner

DISPENSING DEVICE

This invention relates to a dispensing device and a method of dispensing comminuted material to, particularly but not exclusively, the respiratory system of an animal such as a mammal or a bird.

As described in for example BG-A-1569707, dispensing devices are known which produce a monodispersed spray or cloud of liquid droplets by a process in which a liquid emerging from an outlet is subjected to an electric field such that the net electric charge in the liquid as the liquid emerges into free space counteracts the surface tension forces of the liquid and the repulsive forces generated by the like electrical charges result in an electrohydrodynamic cone or jet which breaks up to form liquid droplets. This process is generally referred to as electrohydrodynamic comminution. The particular device described in GB-A-156707 is intended primarily for crop spraying and is an inherently bulky, though portable, device. The droplets produced by this device are charged close to their Rayleigh Limit and thus in use migrate quickly toward wet conductive surfaces. Accordingly, such a device would not be suitable for delivery of liquid droplets to an animal respiratory system because the charge on the droplets would cause them to migrate quickly toward the wet conductive surfaces in the mouth rather than to pass to the upper respiratory tract.

GB-A-2018627 describes an electrohydrodynamic spray device wherein a charged droplet spray produced at a comminution site is fully or partially electrically discharged by means of a discharge electrode in the form of a sharp or pointed edge which is located downstream of the comminution site. Thus, in operation of this device, an electrical potential applied to the discharge electrode causes the discharge electrode to generate gaseous ions by corona discharge. The gaseous ions are then attracted to the oppositely charged droplets of the spray produced by the comminution site and fully or at least partially discharge the liquid droplets. GB-A-2018627 thus effects at least partial discharging of the liquid droplets by ion bombardment.

Unfortunately, ion bombardment discharging may interfere with the comminution process and may reduce the quality and reliability of the liquid droplet spray. Indeed, the detrimental affect on ion bombardment on the comminution spray has been observed in laboratory experiments. In order to counteract these detrimental effects, EP-A-0234842 proposes the use of an annular shield electrode which is positioned between the comminution site and the discharge electrode and aims to maintain a steady electrical field at the comminution site and to shield the comminution site and resulting liquid droplet spray from ions crated at the discharge electrode downstream of the comminution jet or spray. The central aperture of the shield electrode needs, of course, to be sufficiently large to allow free passage of the charged droplets but also small enough to hinder ions from travelling around the spray cloud and interfering with the electrohydrodynamic cone or jet. Experiments have, however, shown that using liquid formulations compatible with human physiology such as water, ethanol and polyethylene glycol, for example, the aperture in the shield electrode must be so large that it is not capable efficiently of hindering the passage of ions as required.

An electrohydrodynamic liquid droplet dispensing device of the kind described in EP-A-0234842 is discussed in a paper entitled "Generation of Micron Sized Droplets from the Taylor Cone" by Meesters et al published in the Journal of Aerosol Science 23 (1992) at pages 37 to 49. The device described in that paper is relatively large being of the order of approximately 150 mm high and 50 mm in diameter. Experiments have shown that if the dimensions of this device are reduced serious stability problems arise. For example, if the current from the discharge electrode is of the same order as the current produced by the charged liquid droplet spray, droplets inevitably impact on the tip of the discharge electrode so seriously reducing the ion current, leading to further droplet impaction and rapid reduction in the overall efficiency of this device. Although such problems could be overcome by increasing the ion current with respect to the electronic current produced by the electrohydrodynamic spray, the ionic wind resulting from air entrainment by the rapidly moving ions produced by the discharge electrode would either cause excessive air turbulence within the device resulting in an unacceptably large proportion of droplets impacting on the interior surfaces of the device or interfere with the electrohydrodynamic cone or jet of the liquid droplet spray causing it to become unstable as well as reducing the monodispersed nature of the spray.

According to one aspect of the present invention, there is provided a dispensing device particularly suitable for use for delivering comminuted material such as liquid droplets to the respiratory system of an animal such as human being, having comminution means for generating an electric field sufficient to produce charged comminuted material from liquid supplied to the comminution means and electrical discharge means for at least partially discharging the comminuted material wherein an ion migration path is provided which does not include the comminution means so that ions produced by the electrical discharge means do not travel to the comminution means until there is a space charge built up by the production of a charged comminuted material spray by the comminution means.

In another aspect, the present invention provides a dispensing device having a geometry such that when a charged spray of comminuted material is produced by electrohydrodynamic comminution means, the resulting space charge diverts ions of opposite charge to the comminuted material away from a path away from the comminution means back towards the comminution means so that the ions may at least partially discharge the spray.

In another aspect, the present invention provides a dispensing device having air-permeable electrically conductive or semi-conductive internal walls through which air is drawn into a comminution area when comminuted material is sucked from the device, so reducing impact of comminuted material within the device and enabling the amount of comminuted material which may be inhaled by a user to be increased.

In another aspect, the present invention provides an electrohydrodynamic dispensing device comprising a flexible or collapsible liquid reservoir which inhibits contact of air with the liquid to be dispensed and acts to retard evaporation of, for example, solvents during storage, thereby increasing the useful lifetime of the device.

In another aspect, the present invention provides a dispensing device which uses a piezoelectric diaphragm pump coupled to an electrical control circuit to provide a steady flow of liquid to electrohydrodynamic comminution means.

In another aspect, the present invention provides a dispensing device wherein valve means are provided at an electrohydrodynamic comminution site to inhibit liquid evaporation when the device is not in use. The valve means may be actuable by, for example, a piezoelectric element and/or by a mechanically, magnetically or electrostatically coupled lever system.

In another aspect, the present invention provides a dispensing device having means for pumping liquid to electrohydrodynamic comminution means. The pumping means may be in the form of a hydraulic syringe having a user-operable piston which may be acted upon by a steady mechanical force provided by, for example, spring biasing means, or may be in the form of, for example, an electro-hydrodynamic pump as described in EP-A-0029301 or an electroosmotic pump such as described in WO94/12285.

In an embodiment where the reservoir is collapsible or has a movable wall the pumping action may be provided by means of a pressure system. The pressure system may be, for example, a spring-loaded pressure system wherein a spring applies a substantially constant pressure onto the reservoir or its movable wall forcing the reservoir to shrink at a substantially constant rate. In another example, the pressure system may be a so-called barrier pack system where the reservoir is located in a pressurised gas container so that the gas exerts a pressure forcing the reservoir to collapse or the movable wall to move to shrink the reservoir. Where such a pressure system is used, then a valve will normally be required at the liquid outlet to prevent leakage.

In another aspect, the present invention provides a dispensing device arranged to produce comminuted material by electrohydrodynamic comminution of liquid supplied to electrohydrodynamic comminution means, wherein means are provided for controlling the flow of liquid to the comminution site, for example the amount of liquid or the rate at which it is supplied, so as to control the amount or dose of comminuted material produced in operation.

In another aspect, the present invention provides a dispensing device having means for applying voltages to electrohydrodynamic comminution means and electrical discharge means in the form of an electromagnetic high voltage multiplier of the type manufactured by Brandenburg or Start Spellman or a piezoelectric high voltage source such as described in, for example, WO94/12285.

The present invention also provides a dispensing device having control means for enabling liquid to be supplied to electrohydrodynamic comminution means prior to actuation of the comminution means and for delaying production of ions from electric discharge means for a predetermined time until a cloud of charged comminuted material has been produced by the comminution means.

Dependent upon the particular liquid, flow rate and applied field, the liquid may solidify or gel or begin to solidify or gel before or after comminution or may remain liquid. Where the liquid solidifies or gels before comminution then a single fibre or short lengths of fibre (fibrils) will result. Where the device is not intended for use as an inhaler the term comminution should be taken to include formation of fibres as well as fibrils and said gel-like or liquid droplets. Where the device is an inhaler then comminution may result in liquid, solid or gel-like droplets or fibrils.

The present invention also provides an inhaler having the features of any one or more of the preceding aspects.

The present invention also provides a method of supplying a medicament to the respiratory system of an animal such as a mammal or a bird using a device having the features of anyone or more of the preceding aspects.

The present invention also provides a dispensing device for delivering electrohydrodynamically comminuted material comprising an olfactory system affecting substance, for example an olfactory repressant or stimulant such as an aroma or perfume or an insecticide, biocide, pesticide, or repressant, insect attractant or repellent or other airborne product.

Embodiments of the present invention will now be described, by way of example, with reference to the accompanying drawings, in which.

Figure 2:
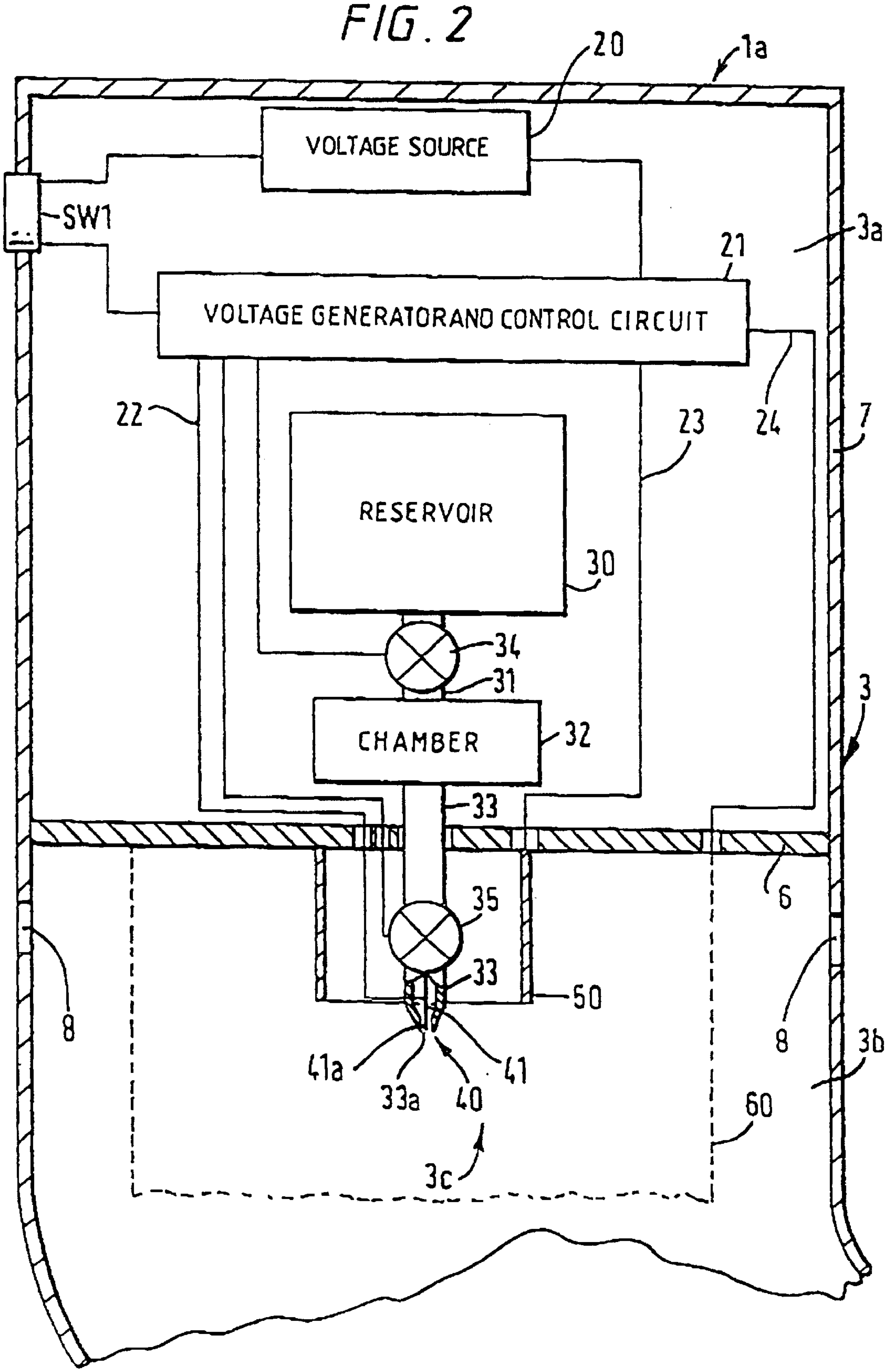
FIG. 2 shows a part-sectional view through one example of a dispensing device embodying the invention illustrating block schematically functional components of the dispensing device.
Figure 3A:
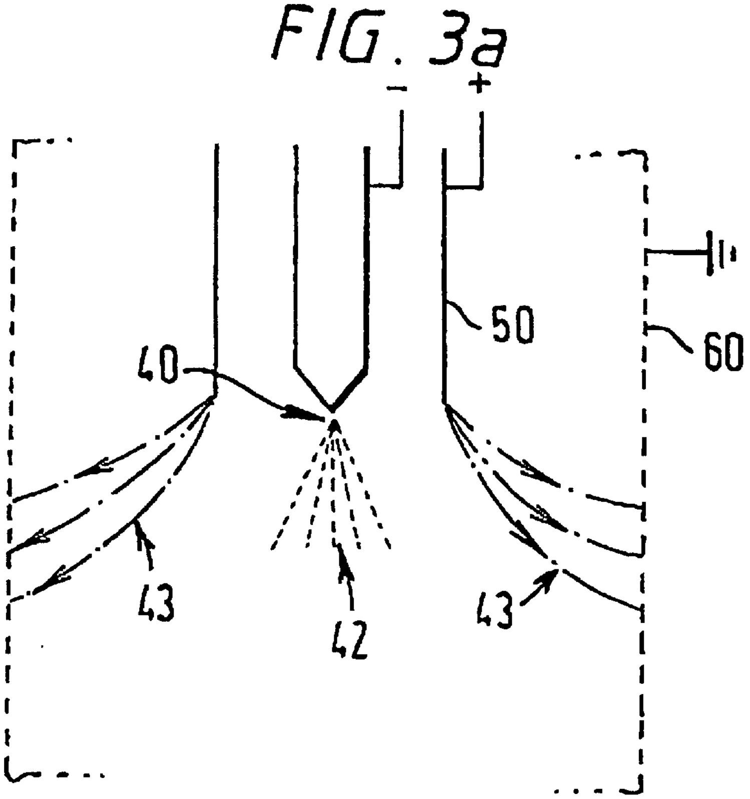
Figure 3B:
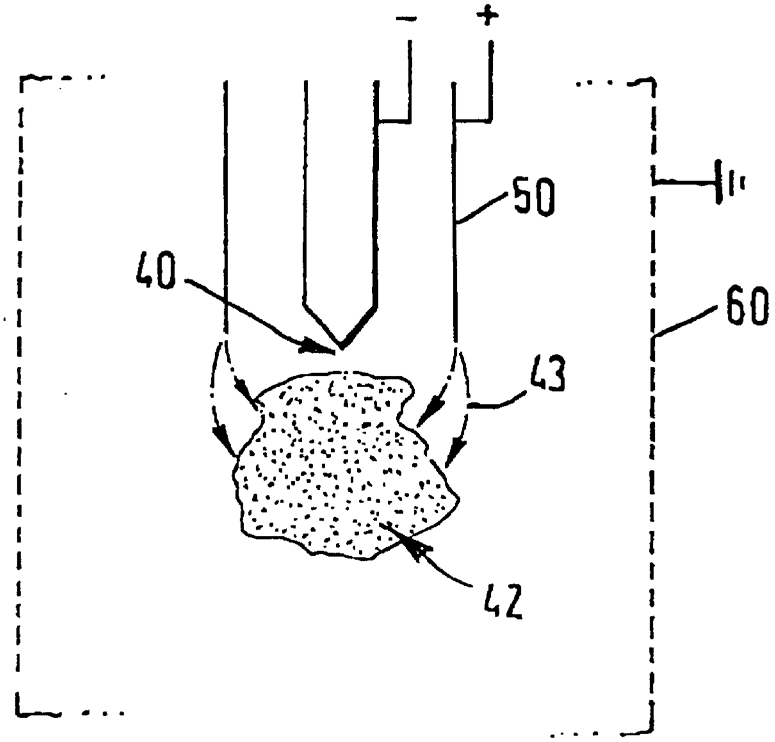
Figure 4:
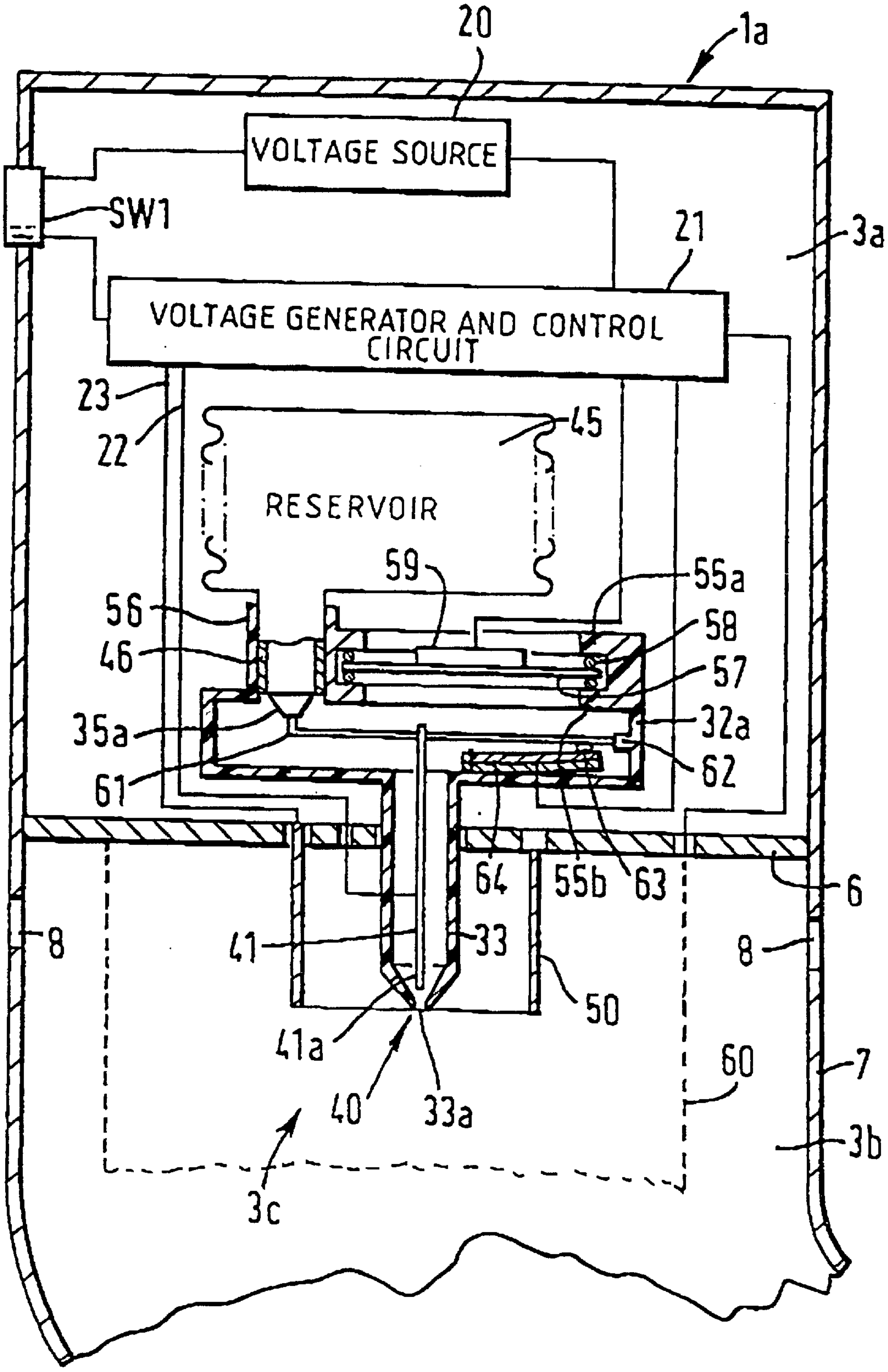
Figure 6B:
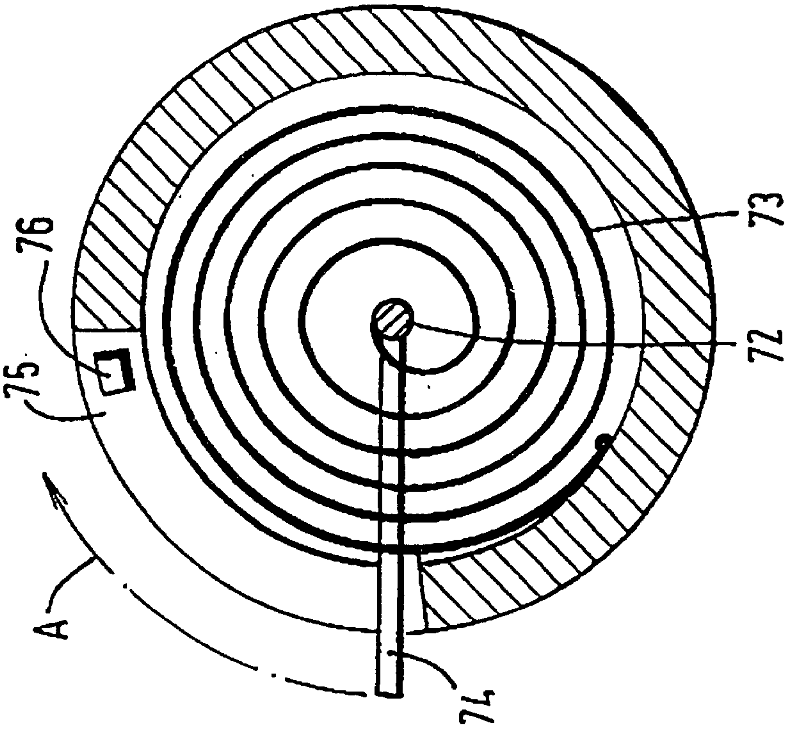
Figure 5:
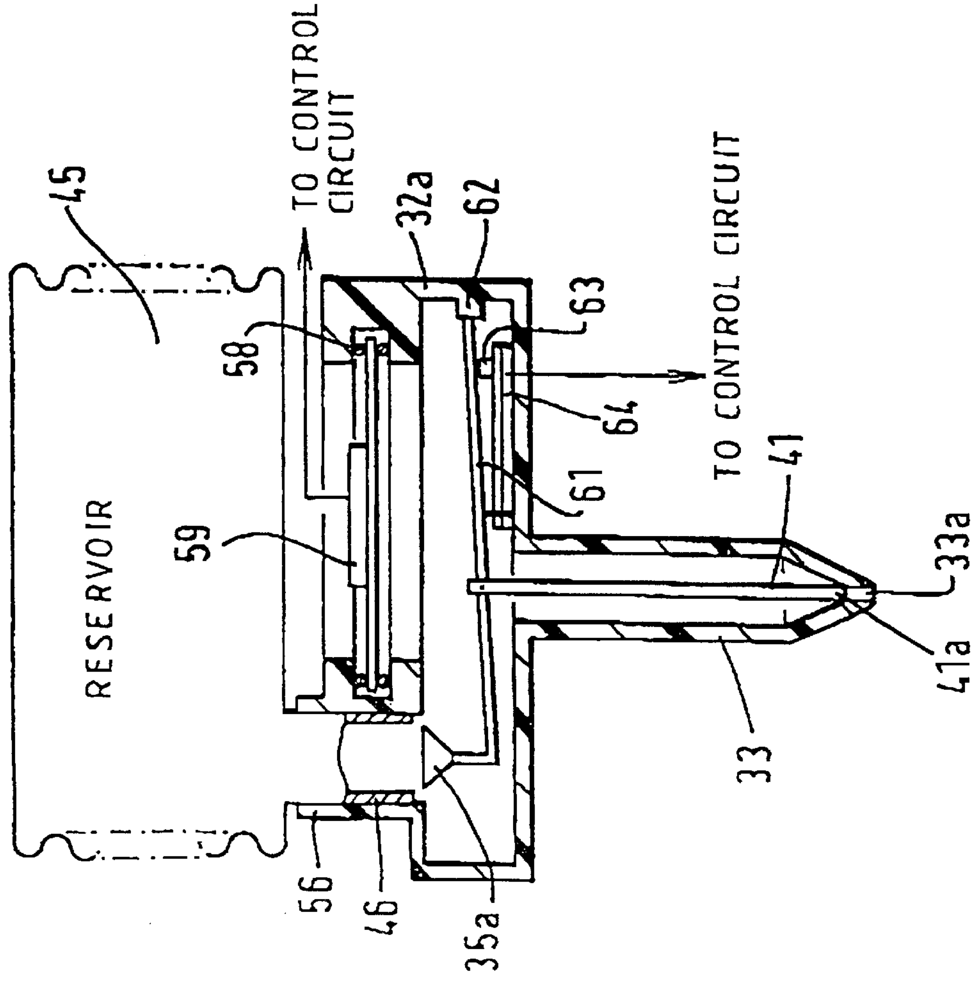
Figure 6A:
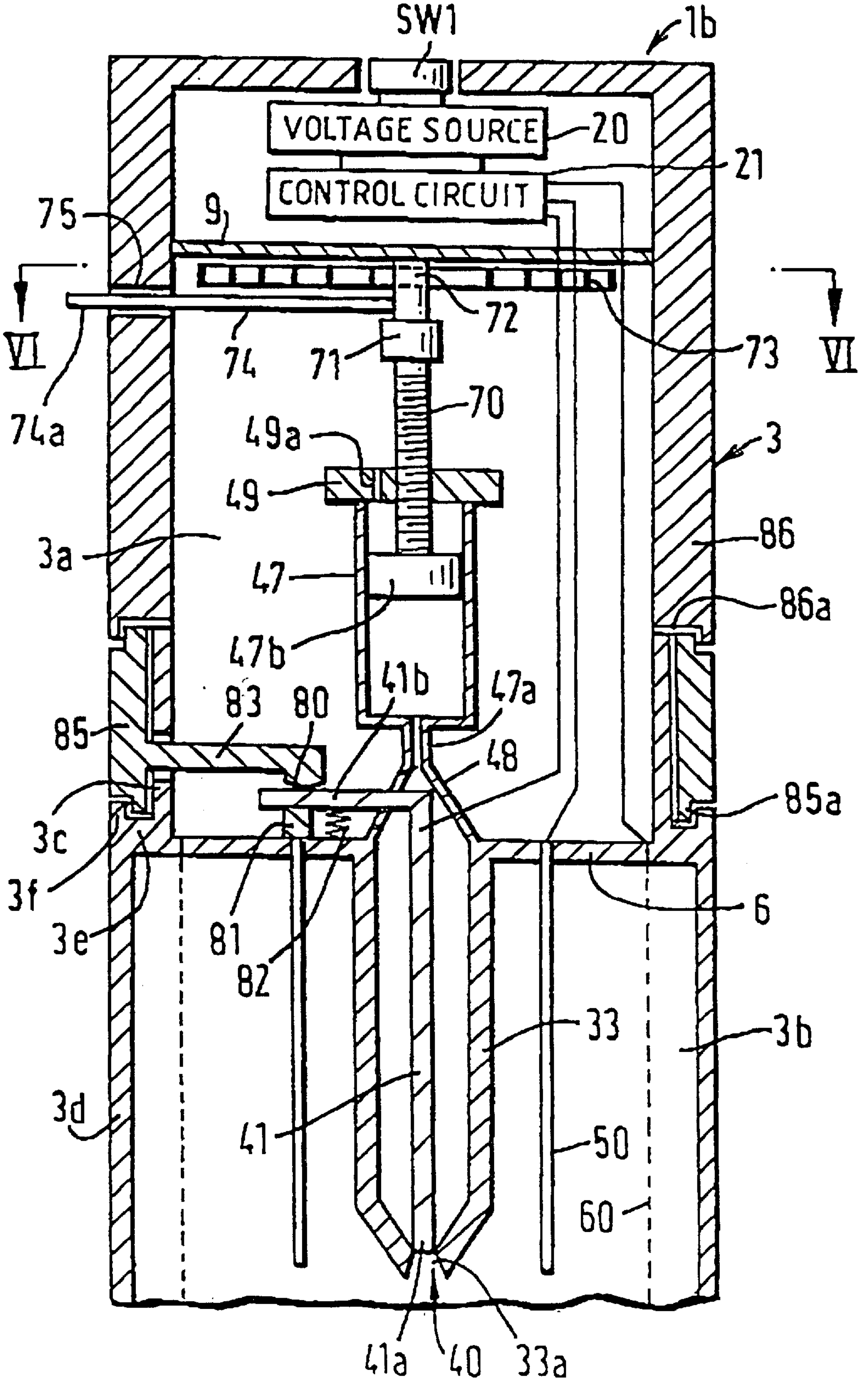

FIGS. 3*a* and 3*b* are schematic diagrams for illustrating the production of charged comminuted material and its subsequent discharge during use of a dispensing device in accordance with the invention;

FIG. 4 shows a part-sectional view similar to FIG. 2 through part of another example of a dispensing device embodying the invention;

FIG. 5 shows a part-sectional view of part of the dispensing device shown in FIG. 4 for illustrating its operation;

FIG. 6*a* shows a part-sectional view similar to FIG. 2 of part of another example of a dispensing device embodying the invention;

FIG. 6*b* is a schematic diagram for illustrating operation of a portion of the device shown in FIG. 6*a;*

Figure 7:
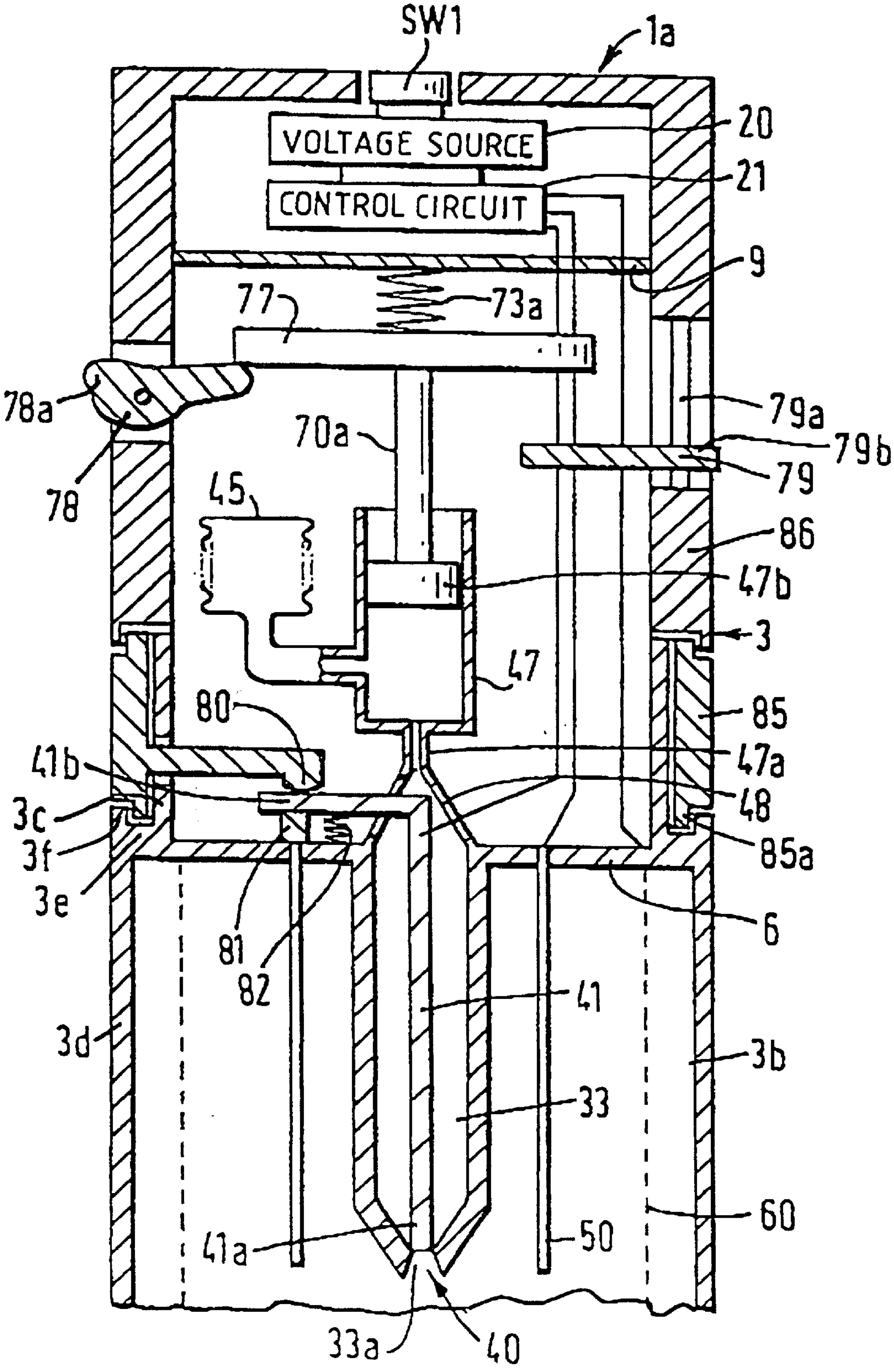
Figure 12:
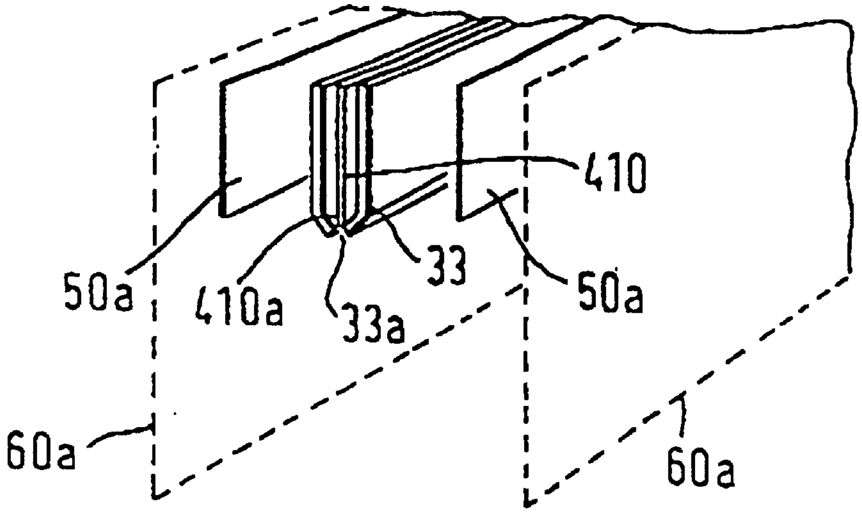
Figure 13:
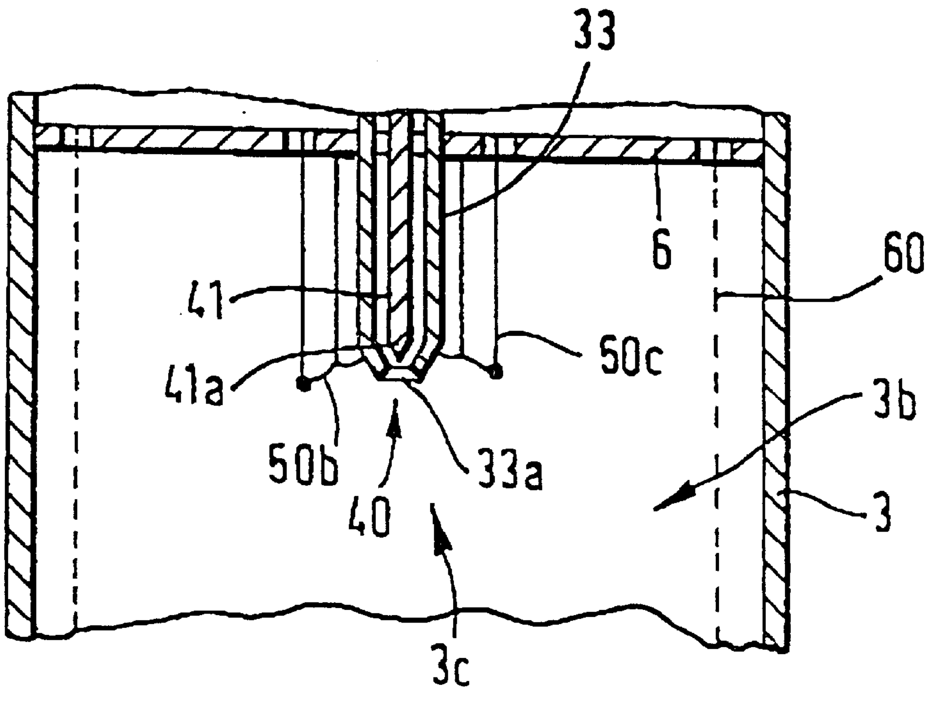
Figure 14:
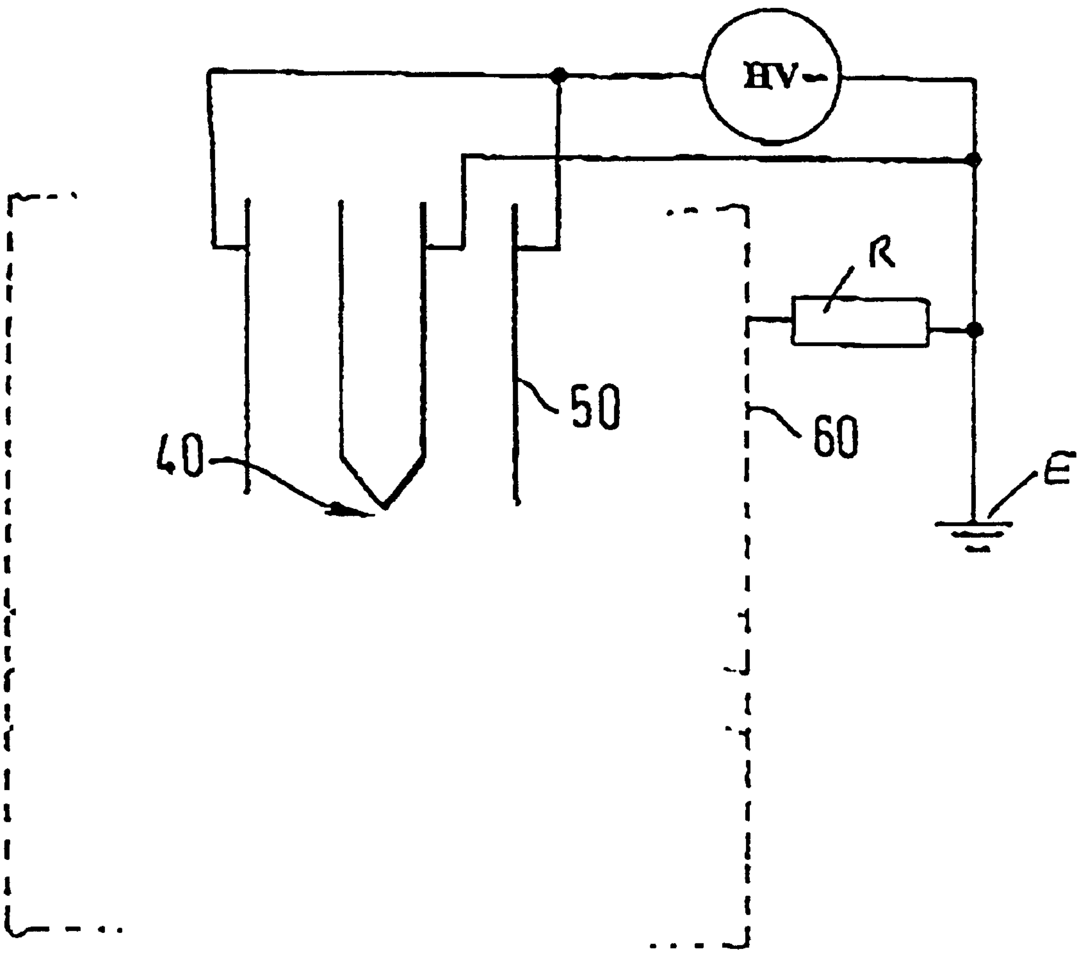

FIG. 7 shows a part-sectional view similar to FIG. 6*a* of part of another example of a dispensing device embodying the invention;

FIGS. 8 to 11 illustrate diagrammatically various forms of comminution site suitable for use in a dispensing device embodying the invention;

FIG. 12 illustrates one possible configuration or arrangement for a comminution site and discharge and further electrodes suitable for a dispensing device embodying the invention;

FIG. 13 illustrates another possible configuration for a comminution site and discharge and further electrodes for use in a dispensing device embodying the invention; and FIG. 14 illustrates by means of a diagram similar to FIG. 3*a* a further modification for a device embodying the invention.

Figure 1:
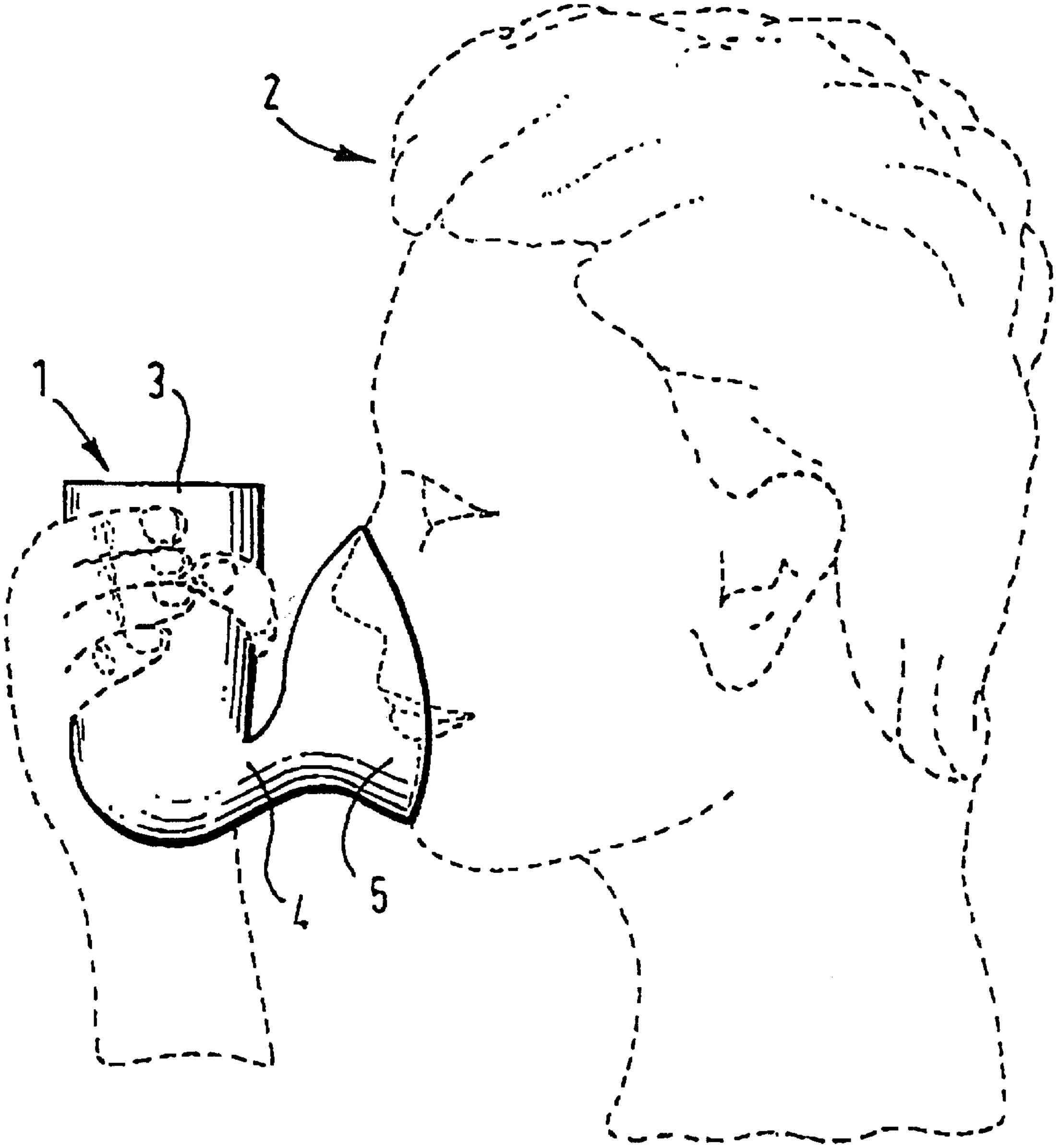
FIG. 1 is a diagrammatic drawing showing a person using a dispensing device embodying the present invention as an inhaler.

As illustrated schematically in FIG. 1, a dispensing device 1 embodying the invention is intended primarily for use as a pocket-size, hand-held inhaler which is actuated manually by a user 2 to enable, for example, delivery of a medicament such as a drug to the upper respiratory tract or lung, for example for delivery of a bronchodilator such as salbutamol or albuterol or steroids such as busenoide for the treatment of, for example, asthma, emphysema or bronchitis.

The dispensing device 1 comprises a housing 3 made of an electrically insulative material such as a plastics material. The inhaler has an outlet 4 through which liquid droplets to be inhaled are supplied to a user. The outlet 4 may be coupled, as shown in FIG. 1, to a mask 5 which covers the nose and mouth of the user to enable both oral and nasal inhalation or may, for example, be coupled to an outlet tube to be received in, placed against or in close proximity to, the mouth of the user where oral rather than nasal inhalation is required or to be received in, placed against or in close proximity to a nostril where only nasal inhalation is required.

FIG. 2 illustrates a part-sectional view through one example of a dispensing device embodying the invention.

As shown in FIG. 2, the housing 3 of the dispensing device 1*a* has an internal wall 6 which separates first and second chambers 3*a* and 3*b* of the housing. The first chamber 3*a* accommodates a voltage source 20 which may be, for example, a conventional battery and a conventional electromagnetic high voltage multiplier of the type manufactured by Brandenburg, Astec Europe, of High Street, Wollaston, Stourbridge, West Midlands DY8 4PG, UK, or Start Spellman of Unit 1, Broomers Park, Broomers Hill Lane, Pulborough, West Suxxes RH20 2RY, UK or a piezoelectric high voltage source such as described in, for example, WO95/32807. The voltage source 20 is coupled to a voltage generator and control circuit 21 which is arranged to derive from the voltage source the various voltages required by the dispensing device as will be described below. Although it may be possible to use a microprocessor or similar control circuit so as to determine the exact value and timings of the various voltages to be described below, in practice a relatively simple control circuit may be used in which one or more resistor-capacitor integrator networks and/or potential dividers are used to smoothly ramp up the voltage to that required. Of course, other known forms of voltage ramping arrangements may be used.

A reservoir 30 of the liquid to be dispensed is coupled via an electrically insulating supply pipe 31 to a chamber 32. The pipe should be made of an insulating material which does not retain charge for any significant length of time. A suitable material is, for example, polyacetyl or Delrin (trade mark). The reservoir may be a collapsible reservoir, for example the liquid may be contained within a flexible collapsible bag, or may have an internal wall arranged to move with the liquid to avoid or at least reduce air contact with the liquid. Liquid may be supplied to the chamber 32 from the reservoir 30 by, for example, gravity feed. Alternatively, the chamber 32 may comprise a pump such as an electrohydrodynamic pump as described in EPO-A-0029301 or an electroosmotic pump of the type described with reference to FIGS. 6 and 7 of WO94/12285 or any other suitable form of electrically operated pump operable under the control of the control circuit 21 so as to enable a steady flow of liquid from the chamber 32.

The chamber 32 is coupled to a liquid supply pipe 33 which passes from the first chamber 3*a* and through the wall 6 into the second chamber 3*b* of the dispensing device.

A comminution site 40 is provided at the end of the supply pipe 33. In this example, the comminution site is provided by the tip 41*a* of an electrically conductive rod 41 which extends axially through the liquid supply pipe 33 so that the tip 41*a* is located adjacent the outlet 33*a* of the supply pipe 33. The electrically conductive rod may have an insulative coating or sleeve so that only the tip 41*a* is exposed.

A discharge electrode arrangement 50 is mounted to the wall 6 so as to extend into the second chamber 3*b* and so as to be spaced from the comminution site 40 in a direction which is generally transverse to the general direction in which liquid issues from the supply pipe 33. The discharge electrode arrangement 50 provides, as will be described below, one or more discharge points or a discharge line which are or is spaced from the comminution site in a direction radially of the supply pipe 33 but located at about the same location as the comminution site in the axial direction of the supply pipe 33. The discharge points may be arranged so as to point in the same direction as the comminution site or may be angled towards the comminution site.

A further electrode 60 is positioned so as to be separated from the comminution site 40 by the discharge electrode 50. In the arrangement shown in FIG. 2, the discharge electrode 50 and further electrode 60 are concentrically disposed with respect to the comminution site so that the discharge electrode 50 surrounds the comminution site 40 and is in turn surrounded by the further electrode 60. The further electrode may extend as far as the outlet 4 of the housing.

The further electrode 60 comprises a perforate electrically conductive or semiconductive body which may, effectively, form an inner wall of the second chamber 3*b* so as to bound a comminution chamber or area 3*a* of the device. For example the further electrode 60 may comprise a tube or cage of wire mesh. The wall 7 of the second chamber 3*b* is formed with one or more apertures 8 to allow air to enter the second chamber 3*b*. The apertures may be symmetrically disposed around the comminution site so as to facilitate a symmetrical air flow.

The comminution sit 40, discharge electrode 50 and further electrode 60 are connected to respective voltage outputs 22, 23 and 24 of the voltage generator and control circuit 21 which is arranged to provide respective voltages so that the voltage applied to the further electrode 60 is intermediate the voltages applied to the comminution site 40 and the discharge electrode 50. In this example, the circuit 21 is arranged to supply a negative voltage to the comminution site 40, a positive voltage to the discharge electrode 50 and earth or ground potential to the further electrode 60. The further electrode 60 has the further advantage of shielding the comminution chamber 3*a* from external electromagnetic fields so that the electrical fields within the device are not detrimentally affected when, for example, the device is held by a user.

The voltage source 20 is coupled to the voltage generator and control circuit 21 by means of a user operable switch SW1 which may be, for example, a conventional toggle or push button switch.

Where desirable, to control dispensing of liquid from the reservoir to the chamber 32, the supply pipe 31 from the reservoir 30 may be coupled to the chamber 32 by means of a valve 34. A further valve 35 may be provided in the supply pipe 33 adjacent the comminution site 40 to inhibit loss of liquid (which loss may occur by evaporation if the liquid being dispensed is volatile) when communition is not occurring.

In the arrangement shown in FIG. 2, the valves 34 and 35 are electrically operated valves, for example solenoid or piezoelectric valves which are operated under the control of the control circuit 21. However it may be possible to use simple one-way mechanical valves and, as will be described below, other mechanical valve arrangements are also possible.

In order to use the dispensing device shown in FIG. 2 as an inhaler, the user 2 places the mask over their nose and mouth, grasps the housing 3 of the dispensing device in their hand as shown schematically in FIG. 1 and actuates the switch SW1 with their thumb or a finger and then breaths in. As will be appreciated, if the device is designed for only oral or only nasal inhalation, the user may place the outlet of the device in, against or in close proximity to their mouth or a nostril. Actuation of the switch SW1 couples the voltage source 20 to the voltage generator and control circuit 21 which supplies a voltage signal to open the valve 34 to allow liquid to be supplied via the chamber 32 and the supply pipe 33 to the comminution site 40. If as discussed above, the liquid is to be pumped from the chamber 32, then the control circuit 21 also supplies the required voltage signals to activate the pump to supply the liquid to the supply pipe 33. At the same time or slightly thereafter, the voltage generator and control circuit 21 outputs the negative and positive voltages on the voltage supply lines 22 and 23 and couples the further electrode 60 to, in this example, earth.

Initially, as shown schematically in FIG. 3*a*, the electric field adjacent the comminution site 40 causes atomization of the liquid supplied to the comminution site so resulting in a spray or jet 42 of charged droplets. As the user breaths in, air is entrained through the apertures 8 in the second chamber 3*b* and through the perforate further electrode 60 into the comminution chamber bounded by the further electrode 60. This general movement of air through the perforate electrode 60 hinders or inhibits charged liquid droplets or other charged comminution products from impacting on the electrode 60. The voltage applied to the discharge electrode 50 results, by corona discharge, in ionization of air or other gas molecules within the second chamber 3*b* to produce ions oppositely charged to the liquid droplets. As shown schematically by the dot-dash lines 43 in FIG. 3*a*, initially the oppositely charged air or gas ions are attracted away from the liquid spray 42 toward the more negatively charged (in this case earthed) further electrode 60. However, as shown in FIG. 3*b*, the space charge resulting from the generation of the liquid droplet spray 42 eventually becomes sufficient to attract the ions away from their normal path and towards the liquid droplet spray 42 so enabling the change on the liquid droplets to be at least partially discharged by the oppositely charged air or gas molecules produced by the discharge electrode 50 so that the liquid droplets breathed in by the user are at least partially discharged.

The use of the further electrode 60 spaced from the comminution site 40 by the discharge electrode 50 enables the discharge electrode 50 to be placed relatively close to the comminution site 40 without the gaseous ions produced by the discharge electrode interfering with the comminution process. Generally, the distance between the discharge electrode and the comminution site will be greater than, for example about twice, the distance between the discharge electrode and the further electrode 60. In practice, the actual relative distances are selected in combination with the respective voltages applied to the electrodes 50 and 60 and the comminution site 40 so as to ensure that gaseous ions are diverted toward the further electrode 60 until a sufficient cloud of charged liquid droplets has been generated and to ensure efficient discharge. Typically, the discharge electrode 50 may be as close as 6–12 mm to the comminution site. This allows the device structure to be particularly compact so that the comminution and discharging arrangement may have, for example, a height of about 40 mm and a diameter of about 30 mm making it particularly suitable for hand-held use and for transportation in a handbag or a user's pocket.

Experiments were carried out using a liquid formulation of 20% by volume polyethylene glycol and 80% by volume ethanol containing typically 2% by mass per volume of Salbutomol with the comminution site 40 being supplied with liquid at a flow rate of 1.33 $\mu$L/s (microliters per second) and being held at a potential of −2.3 kilovolts, with four discharge electrodes 50 held at a potential of +2 kilovolts spaced at 90° intervals around the circumference of a 15 mm diameter circle centered on the comminution site 40 and an earthed 25 mm diameter cylindrical perforate electrode 60 concentrically arranged with respect to the comminution site. The liquid droplets emerging from the outlet 4 of the device were found to be substantially uncharged and a device efficiency of over 97% (that is the percentage of the mass of drug supplied to the comminution site that is actually delivered to the outlet 4 of the device) was observed.

Charged liquid droplets produced by electrohydrodynamic comminution have a charge-to-mass ratio corresponding roughly to the Rayleigh Criterion for charged droplet stability, namely:

$$r = \left[\frac{q^2}{32\pi^2\epsilon\gamma}\right]^{1/3}$$

where r is the droplet radius in meters, $\epsilon$ is the relative permittivity, $\gamma$ is the liquid's surface tension, and q the charge on the droplet. Accordingly by controlling the voltage applied to the comminution site, the charge and thus the radius of the liquid droplet can be controlled.

The discharge electrode arrangement may be arranged either to fully or partially electrically discharge the charged liquid droplets by adjusting the voltage applied to the discharge electrode in accordance with the voltage applied to the comminution site and the resistivity and flow rate of the liquid being comminuted s that the number of ionised air molecules produced by the discharge electrode is sufficient to either fully or partially discharge the comminuted material.

FIG. 4 is a part-cross sectional view similar to FIG. 2 showing part of another example of a dispensing device 1*a* embodying the invention.

The dispensing device shown in FIG. 4 has a voltage source 20, voltage generator and control circuit 21, comminution site 40, discharge electrode 50 and further electrode 60 which are arranged in and operate in a similar manner to the corresponding components described with reference to FIG. 2 when the switch SW1 is operated by a user in the manner discussed above.

The dispensing device shown in FIG. 4 differs from that shown in FIG. 2 in the manner in which a liquid to be dispensed is supplied to the comminution site 40. In the arrangement shown in FIG 4, liquid to be dispensed is retained in a collapsible reservoir 45 which may be in the form of a flexible bag or may have a bellows type arrangement. The collapsible reservoir 45 has an outlet pipe 46 which is received in a fluid-tight manner within an inlet pipe 56 of a pump chamber 32*a* which may be integrally formed with, for example moulded with, the supply tube 33 for supplying liquid to the comminution site 40.

A flexible diaphragm 57 is mounted in a fluid-tight manner into an aperture in an upper portion of the pump chamber 32*a*. The periphery of the flexible diaphragm 57 is, in the arrangement shown, held between twin flanges 55*a* and 55*b* bounding the aperture. O-ring or similar seals 58 may be provided to ensure a fluid-tight seal. In an alternative arrangement, where the pump chamber 32*a* is moulded from a plastics material, for example, the flexible diaphragm may be positioned in place during the moulding process.

The flexible diaphragm is caused to flex under the control of a diaphragm control member 59 when a voltage supplied by the control circuit 21 to the diaphragm control member 59 reaches a predetermined value. The diaphragm control member 59 may be, for example, a piezoelectric element formed by a ceramic disc on a metal plate such as is available commercially from Morgan Matroc Ltd., of Bewdley Road, Stourport-on-Severn, Worcestershire DY13 7QR, UK. Of course, other means for causing the diaphragm 57 to flex, for example, a piston arrangement of a magnetically or electrostatically coupled lever system may be used.

As shown in FIG. 4, the conductive rod 41 which provides the comminution site 40 is pivotally mounted to and depends from a support arm 61 which is pivotally mounted at one end to a pivot mount 62 provided on an inner wall of the pump chamber 32*a*. The other end of the support arm 61 carries a valve member 35*a* for closing the outlet pipe 46 from the flexible reservoir 45. The support arm 61 is supported adjacent the pivot mount 62 by a support bar 63 which itself is mounted at one end of a piezoelectric element 64 having its other end fixedly secured to a base wall of the pump chamber 32*a*. In this case, the piezoelectric element 64 will normally have a thin and flexible resistive coating to insulate it from the liquid in the pumping chamber. The piezoelectric element 64 preferably comprises a piezoelectric bimorph formed of a plurality of layers of ceramic which provides a greater degree of movement for a given applied voltage than a single piezoelectric ceramic layer. Such piezoelectric bimorphs are also commercially available from Morgan Matroc.

Prior to use of the dispensing device shown in FIG. 4, no voltage is applied to either of the piezoelectric element 64 and diaphragm control member 59. In this state, as shown in FIG. 5, the tree and 41*a* of the conductive rod 41 cooperates with a narrowing portion of the insulative supply pipe 33 to form a valve head closing the outlet 33*a* of the insulative supply pipe to prevent loss of liquid by evaporation. The valve head 35*a* is spaced away from the outlet 46 of the flexible reservoir 45 allowing the pump chamber 32*a* to be filled with liquid.

When the switch SW1 is actuated by the user and the voltage supplied by the control circuit reaches the required value, the piezoelectric element 64 flexes or bends so raising the rod 41 to cause the valve head 35*a* to close the outlet pipe 46 of the reservoir 45 and to move the free end of the rod 41 away from the outlet 33*a* of the supply pipe 33 to bring the device into the condition shown in FIG. 4. When the voltage supplied to the piezoelectric element 59 reaches a predetermined value, the piezoelectric element 59 causes the diaphragm 57 to flex downwardly in FIG. 4 so forcing the liquid in the pump chamber 32*a* to flow toward the outlet of the supply pipe 33 at a steady flow rate. The voltage generator and control circuit 21 applies voltages to the comminution site 40, discharge electrode 50 and further electrode 60 in the same manner as described with reference to FIGS. 2, 3*a* and 3*b* so resulting in a spray of charged droplets which are then discharged by the discharge electrode 50 and pass, by the action of the user breathing in, through the outlet 4 of the device into the upper respiratory system of the user. As discussed above, the control circuit may be a microprocessor or resistor-capacitor RC network control circuit.

FIG. 6*a* shows a part-cross sectional view similar to FIGS. 2 and 4 of part of another dispensing device embodying the invention.

In the arrangement shown in FIG. 6*a*, liquid to be dispensed is contained in a syringe 47 having its capillary tube outlet 47*a* coupled to a liquid guiding funnel arrangement 48 for guiding liquid to the liquid supply pipe 33 which is, in this example, mounted to or integrally formed with the wall 6 dividing the first chamber 3*a* from the second chamber 3*b*.

The syringe body 47 is mounted to a nut 49 provided with an air vent 49*a*. Although not shown, the nut is itself secured in a conventional manner to the wall of the upper or first chamber 3*a*. The syringe piston 47*b* is carried by a screw-threaded rod 70 which extends through and cooperates with the nut 49.

The other end of the screw-threaded rod 70 is coupled by a uni-directional coupling 71 of conventional form to a shaft 72 rotatably mounted to an internal wall 9 of the housing which separates the voltage source 20 and control circuit 21 from the remainder of the device. A flat coil spring 73 has one end secured to shaft 72 and the other end secured to the inner surface of the housing. A level 74 is fixed to and extends from the shaft 72. A free end 74*a* of the lever extends through a slot 75 provided in the housing so that the free end 74*a* of the lever 74 can be gripped by a user. The lever 74 is movable within the slot 75 as will be described below to enable a user to wind up the spring 73.

A cam surface 80 retains an end 41*b* of the rod 41 on a support 81 against the action of a biasing spring 82 so as bias the other end 41*a* of the rod 41 into a position closing the outlet 33*a* of the liquid supply pipe 33.

The cam surface 80 is provided on a rod 83 which extends through an aperture in the housing 3 from an outer rotatable sleeve 85.

The portion 3*c* of the housing forming part of the side walls of the first chamber 3*a* is recessed with respect to the portion 3*d* forming the side walls of the housing forming the second chamber 3*b* and has at its lower end a radially outwardly extending flange 3*e* provided with a lip 3*f* which receives an axially extending rim 85*a* of the sleeve 85.

The upper end of the sleeve 85 is held in place by a separate cap member 86 forming a top part of the upper chamber and having a recess 86*a* for receiving an axially extending circumferential projection of the sleeve. The cap member may for example be secured to the housing portion 3*c* by adhesive.

Operation of the device shown in FIG. 6*a* will now be described with the aid of FIG. 6*b* which shows very schematically a cross-sectional view of the device of FIG. 6*a* taken along line VI—VI in FIG. 6*b*. For simplicity FIG. 6*b* omits all components of the device apart from the coil spring 73, the shaft 72 to which one end of the spring 73 is attached, the lever 74 and its associated aperture 75 and a stop 76. The user first primes the device by rotating the lever 74 in its slot 75 in the direction of the arrow A in FIG. 6*b* and against the biasing force of the coil spring 73 so winding up the coil spring. The unidirectional coupling 71 prevents rotation of the piston rod 70 as the spring is being wound up. The stop 76 is mounted within the aperture 75 so as to engage the lever when the lever meets the stop. For example, the stop 76 may comprise a spring-biassed detent which engages the lever as it rides over the stop. Once the spring has been wound up, the user rotates the sleeve 85 causing the cam surface 80 to move relative to the end 41*b* of the rod 41 to allow the biasing spring 82 to move the rod 41 upwardly in FIG. 6*a* so as to open the outlet 33*a* of the liquid supply pipe 33. An opening is provided in the funnel arrangement 48 to enable movement of the rod 41.

Actuation of the switch SW1 provided in the top of the cap 86 of the housing causes the control circuit to supply the required voltages to the electrodes 41, 50 and 60, as discussed above, the user then depresses a button (not shown) to release the engagement between the detent 76 and the lever 74 allowing the coil spring 73 to twist the threaded shaft of the piston rod 70 through a set angle at a set rate so that the cooperation between the piston rod 70 and nut 49 causes the piston 47*b* to move through the syringe 47 so that a metered amount of liquid is supplied at a steady rate from the syringe to the liquid supply pipe 33. The air vent 49*a* in the nut 49 enables air to enter the syringe to allow movement of the piston 47*b*.

Liquid passing from the outlet 33*a* of the supply pipe 33 is atomized or comminuted by the electric field at the comminution site 40 and, once sufficient space charge has built up, the charge on the thus produced droplets is electrically discharged by ions generated by the discharge electrode 50 as described above so providing a cloud or spray of discharged droplets which can then be inhaled by the user.

The lever 74 may be mechanically and/or electrically connected to the switch SW1 so that depression of the switch SW1 also causes the lever to be released to allow the spring 73 to move the piston, so obviating the need for a separate button.

Once the dose of liquid has been supplied from the outlet 33*a* of the supply pipe 33, the user rotates the sleeve 85 to return the rod 41 to its position closing the outlet 33*a* of the liquid supply pipe 33.

The above described actions are repeated each time the user wishes to use the device and with each use the piston 47*b* moves further down the syringe delivering a metered dose each time to the supply pipe 33.

It will of course, be appreciated that alternative ways of priming the coil spring or biassing the piston to cause a metered does to be delivered to the supply pipe 33 may be used.

FIG. 7 is a part cross-sectional view similar to FIG. 6*a* of part of a further example of a device embodying the invention.

The device shown in FIG. 7 is identical in operation to that shown in FIG. 6*a* except in the manner in which liquid is supplied to the supply pipe 33. In the device shown in FIG. 7, the syringe 47 has a reciprocable piston 47*b*. The free end of the piston rod 70*a* is mounted to a support plate 77 which is held in a first position against the biassing action of a spring 73*a* by a spring-biassed latch 78. The latch 78 is pivotally mounted to the housing 3 and has a portion 78*a* extending through an aperture in the housing 3 to form a user operable switch so that when, after having rotated the rotatable sleeve 85 to open the outlet 33*a* and actuated the switch SW1, the user presses downwardly on the portion 78*a* the latch 78 is pivoted upwardly past the edge of the support plate 77 thus freeing the support plate and allowing it to move downwardly under the action of the spring 73*a* until the plate 77 meets a support member 79. This causes the piston to supply a metered dose of liquid to the outlet 33*a* where the liquid is electrohydrodynamically comminuted as described above. The actual amount of the dose supplied is determined by the location of the support member 79.

The support member 79 is slidably mounted in a slideway 79*a* defined in the wall of the housing 3 and in order to reprime the device, the user grasps a free end 79*b* of the support member 79 and moves it upwardly in the slideway 79*a* so causing the support plate 77 to move upwardly in FIG. 7 forcing the latch 78 to pivot upwardly against its spring biassing so that the support plate 77 comes to rest on the latch 78 as shown in FIG. 7. During this return movement, the liquid in the syringe is replenished by supply through a one-way valve (not shown) from a collapsible reservoir 45 of similar type to that shown in FIG. 4.

It will be appreciated that any suitable form of biassing and latching mechanism may be used to control movement of the piston in the device shown in FIG. 7. In addition, the device shown in FIG. 6*a* may be modified so as to provide a reciprocating piston arrangement by removing the unidirectional coupling and providing the collapsible reservoir 45.

It will, of course, be appreciated that other mechanical lever arrangements may be used to control opening of the liquid supply valve and priming and releasing of the spring mechanism for rotating the piston rod. Also a magnetically coupled or electrostatically coupled lever system may be used.

A combination of electrically and mechanically operated arrangements may be used so that, for example, a mechanical outlet valve of the type shown in FIGS. 6*a* and 7 may be used in combination with an electrically operated outlet valve or alternatively an electrical pumping arrangement may be used with a mechanical outlet valve.

In the arrangements shown in FIGS. 2, 4, 6*a* and 7, the comminution site is provided by a rod 41 which extends through the liquid supply pipe 33 and cooperates with the liquid supply pipe so as to form a valve closing the liquid supply pipe opening 33*a* when supply of liquid from the liquid supply pipe is not required.

Figure 8:
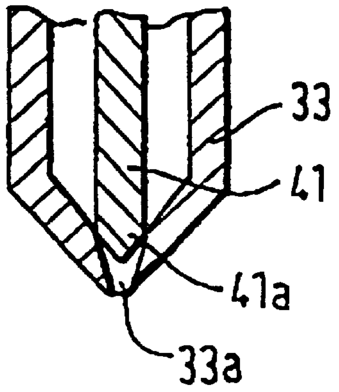

The end 41*a* of the rod 41 and the opening 33*a* of the liquid supply pipe 33 may be shaped so as to improve the liquid tightness of the valve when closed. For example, as shown in FIG. 8, the rod 41 may be provided with a conical, i.e. sharpened or pointed, end 41*a* and the opening 33*a* of the liquid supply pipe may be arranged to be frusto-conical, narrowing towards the exterior so that, when the valve is closed, the conical end or tip 41*a* of the rod extends into the outlet opening of the liquid supply pipe.

Figure 9:
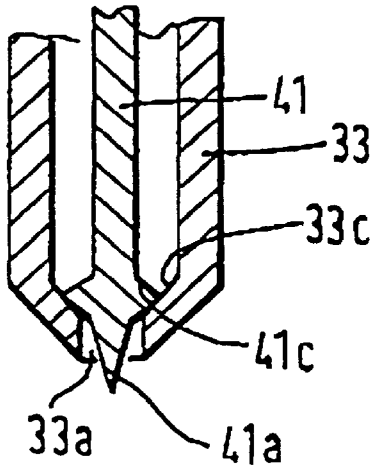

FIG. 9 shows a further alternative arrangement wherein the rod 41 is provided with a radially extending flange 41*c* which, when the valve is closed, rests on a cooperating surface 33*c* of the outlet of the liquid supply pipe.

Figure 10:
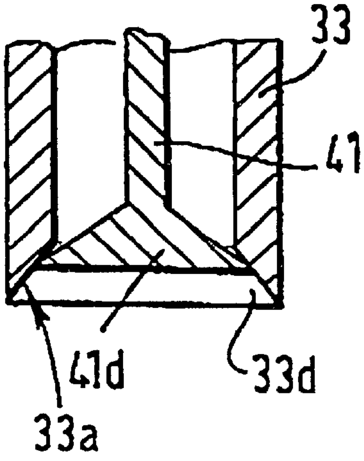

FIG. 10 shows a further possible arrangement which may be used in the devices shown in FIGS. 2, 6*a* and 7 wherein the rod 41 carries a conical valve head 41*d* which cooperates with a frusto-conical valve seat 33*d* provided by the opening 33*a* of the liquid supply pipe 33. In this arrangement, the rod 41 is raised so as to close the valve and lowered to open the valve, and so would require the operation of the cam surface 80 on the biasing spring 82 shown in FIG. 6*a* and 7 to be reversed.

Figure 11:
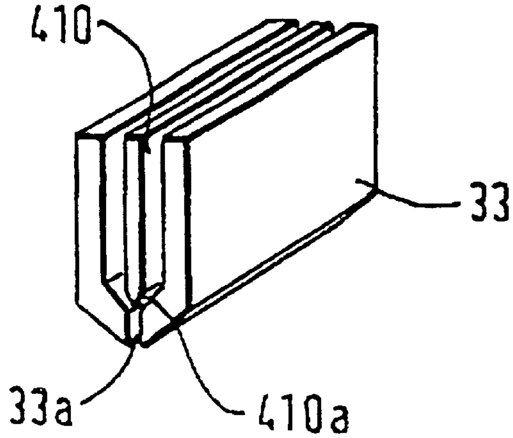

In the arrangement described above, the comminution site is provided as a point by a cylindrical rod 41 However, other forms of comminution site may be used as described in, for example, WO95/26235, WO95/26234 or WO95/32807. As one example, the comminution site may be provided as a ring or annulus of spaced-apart comminution points each similar to the one shown in FIG. 1 as described with reference to FIG. 5 of WO95/32807. As another possibility, as illustrated schematically in FIG. 11, the comminution site 40 may be provided as a line rather than a point or series of points by replacing the rod 41 described above by a planar member 410 providing at its lower end a comminution site in the form of a knife edge 410*a* along which multiple jets will be formed in use. As another possibility an annular comminution site may be used by providing a hollow cylinder in place of the rod 41.

Where the comminution site itself is rotationally symmetrical, for example where the comminution site comprises a rod or cylinder, then the discharge electrode or electrode and the further electrode will preferably be rotationally symmetric and concentrically arranged with respect to the comminution site. Where, however, the comminution site is provided as a linear edge as shown in FIG. 11, then the discharge electrode may similarly be provided as two elongate edges 50*a* as shown in FIG. 12 and the further electrodes may be provided by two perforate planar members 60*a* disposed either side of the comminution site so as to ensure that, in use, the generated electric fields are symmetric with respect to the comminution site.

As discussed above, the discharge electrode may be formed as a single discharge point or may be formed by a number of discrete discharge points which may be provided by, for example, separate discharge needles or may be provided by a discharge wire 50*b* held in place by conductive restraints 50*c* as shown schematically in FIG. 13.

In the arrangements described above, liquid is supplied to the comminution site by gravity feed or by a pumping mechanism such as a flexible diaphragm or a syringe pump. As discussed above, other pumping mechanisms may be used, for example, an electrohydrodynamic pump such as that described in EP-A-0029301 or an electroosmotic pump as described with reference to FIGS. 6 and 7 of WO94/12285 may be used or other forms of pump which allow a metered dose to be supplied may be used.

In an embodiment where the reservoir is collapsible or has a movable wall the pumping action may be provided by means of a pressure system. The pressure system may be, for example, a spring-loaded pressure system wherein a spring applies a substantially constant pressure onto the reservoir or its moveable wall forcing the reservoir to sharing at a substantially constant rate. In another example, the pressure system may be a so-called barrier pack system where the reservoir is located in a pressurised gas container so that the gas exerts a pressure forcing the reservoir to collapse or the movable wall to move to shrink the reservoir. Where such a pressure system is used, then a valve will normally be required at the liquid outlet to prevent leakage.

In the examples described above, the further electrode 60 is perforate and is spaced from the interior wall of the housing so as to enable air flow through the further electrode to inhibit impact of comminuted material or product on the further electrode. It may, however, be possible to provide the further electrode by providing an electrically conductive or semiconductive coating on the interior wall of the housing and to rely on air flow over the coating to inhibit impact of comminuted product on the further electrode. In such an arrangement, at least a major part of the interior wall of the housing may be coated and earthed which should enable particularly efficient electromagnetic shielding but at the expense of there being an increased likelihood of deposition of comminuted product onto the further electrode and thus less efficient delivery of the comminuted product.

The dose delivered by a device embodying the invention may be adjustable. For example, in the devices shown in FIGS. 2 and 4, the relative times at which the valves 34 and 35 in FIG. 2 and 35*a* and 41*a* in FIGS. 4 are opened may be used to control the amount of liquid delivered to the communication site. This may be achieved by, for example, adjusting the rates at which the respective voltages are ramped up to the required voltages to actuate the valves by appropriate adjustment of the control circuit. Such adjustment may be carried out at a factory level by adjusting the values of the resistors and capacitors in the ramp circuit or may be controllable by a pharmacist or an end user by providing switch means for switching in or out additional resistors and capacitors to adjust the voltage ramp rates.

In the device shown in FIGS. 6*a* and 6*b,* the amount by which the spring is wound up or allowed to unwind, and so the amount by which the piston moves within the syringe cylinder, may be selected by determining the circumferential extent of the slot 75 and/or the location of the abutment 76. The location of the abutment 76 may be selectable by a pharmacist or a doctor to adapt the device for the particular requirements of a particular patient or may be selectable by a patient to enable the patient to select the number of doses required. For example, the slot 75 may be provided with a number of different discrete locations to which the abutment 76 may be moved with each location being identified by a scale on the housing as providing a given multiple of a basic dose. Where the location of the abutment 76 and therefore the dose is selectable by the pharmacist or doctor, then the abutment may be designed so as to be fixed in position once inserted into the slot and may be, for example, colour coded to enable easy identification of the dose the device is designed to delivery.

In the device shown in FIG. 7, the delivery dose may be adjusted by, for example, adjusting the length of the slideway 79*a* in the factory or by providing on the slideway an abutment similar to the abutment 76 shown in FIG. 6*b* which may be located as discussed above.

Enabling the dose of liquid delivered to the comminution site to be controlled allows the device to be adapted for different patient requirements. Thus, for example the device may be adapted for use by an adult or a child and also for use with different drugs which may require different liquid dosages.

In the examples described above, the voltage applied to the further embodiment 60 is arranged to be intermediate the voltages applied to the comminution site 40 and the discharge electrode 50. This requires, if one of the three electrodes is at earth or ground potential, two reference voltages. FIG. 14 illustrates diagrammatically a modification which may be applied to any of the devices described above. In the arrangement shown in FIG. 14, the discharge electrode or electrode 50 is/are coupled to a potential HV- which is negative with respect to the potential applied to the comminution site 40. In the example shown, the comminution site 40 is earthed (ground potential) and the further electrode 60 is coupled to earth via a resistance R. Typically, a voltage of about −6 Kv may be applied to the discharge electrode(s) 50 and the resistance R may be approximately 600 Megaohms.

When the negative voltage HV- is first applied, ions generated by the discharge electrode(s) 50 migrate directly toward the further electrode 60. The further electrode or cage 60 itself discharges through the resistance R causing the potential difference between the further electrode and the discharge electrode 50 to drop thereby limiting the production of ions by the discharge electrode 50. As the potential at the further electrode 60 changes, the potential difference between the comminution site 40 and the further electrode increases inducing comminution of liquid supplied to the comminution site 40.

The system is self-equilibrating. Not only does the potential of the further electrode 60 adjust the flow of ions from the discharge electrode 50 but also the space charge produced by charge comminuted matter issuing from the comminution site can increase the ion production as required.

Where the dimensions of the device are as described above, the discharge electrode(s) is at −6 Kv, the resistance R is roughly 600 Meaohms and the current through the further electrode is roughly 5 microamps, then the potential reached by the cage or further electrode 60 at equilibrium will be approximately 3 Kv which is ideal.

In the arrangement shown in FIG. 14, negative ions/electrons are used to discharge the positively charged comminuted matter produced at the comminution site 40. This enables rapid response and allows the system to reach equilibrium rapidly. However, the arrangement shown in FIG. 14 may be modified so as to work with positive ions by using a positive high voltage source in place of the negative high voltage source HV- and by reducing the resistance R to compensate for the fact that, where positive ions are used as the discharging means, their production is indirect, that is not due to electron emission at the discharge electrode but by virtue of an avalanche effect in towards the electrode.

Typically, liquids with resistivities in the range of from $10^2$ to $10^6$ ohm-metres and viscosities in the range of from 1 to 250 centipoise may be comminuted by a device embodying the present invention. The liquid may be a melt, solution, suspension, emulsion microsuspension or microemulsion or even a gel provided that the liquid can be caused to flow at an adequate flow rate to the comminution site.

The size of the comminuted liquid droplets produced depends on, for a given liquid, the electric field used to cause comminution and the flow rate. In the example given above, the electric field used for causing comminution and the flow rate of the liquid being comminuted are selected to produce droplets of a size suitable for delivery to the upper respiratory tract. However by appropriately selecting the flow rate and the electric field for a given liquid, droplets of a size suitable for delivery to the mouth cavity and throat area or to the nasal passages or even the small bronchi of the lungs may be provided.

As discussed above, a dispensing device embodying the invention is primarily intended for use as a hand held portable device suitable for use as an inhaler for supplying a medicament to the respiratory system. Medicaments suitable for delivery by a device embodying the invention include bronchodilators or steroids as discussed above and others for treatment of disorders of the upper respiratory tract including disorders of the nasal mucosa and congestion and disorders of the upper respiratory tract associated with hayfever.

Particular medicaments for use as nasal decongestants include as oxymetazoline, xylometazoline, phenylephrine, propylhexadrine, nephazoline and tetrahydrozoline and as appropriate salts thereof such as the hydrochloride salt, and formulation thereof.

A device embodying the invention may also be suitable for oral or nasal delivery of drugs which are currently being tested as anti-migraine agents such as the triptans (for example almotriptan, eletriptan, naratriptan, rizatriptan, sumatriptan and zolmitriptan) or CP-122, 288 produced by Pfizer and Lanepitant produced by E. Lilley. A device embodying the invention is suitable for use as a pocket-size hand held inhaler for, for example, the occasional delivery of a medicament because its design enables the electrical discharge means and comminution site to be brought close together without impeding their function so allowing the device to be compact. The device should also be user friendly in that it is simple to operate, particularly for unskilled users and the infirm, because the liquid droplet spray is delivered under the control of the inhalation of the user and not with the force of a gas discharge as in conventional aerosol systems.

A device embodying the invention may however also be used for dispensing droplets of other liquids, for example as a desktop or hand-held dispenser for dispensing olfactory system, affecting substances, for example olfactory represents or olfactory stimuli such as aromas and perfumes; insect repellents or attactants, biocides or insecticides, pesticides and other airborne products.

What is claimed is:

1. A dispensing device, comprising:

comminution means for subjecting liquid to an electric field for causing comminution of the liquid to produce charged comminuted material;

liquid supply means for supplying liquid to the comminution means;

electrical discharge means for producing ions to at least partially electrically discharge comminuted material produced by the comminution means and ion attracting means spaced from the comminution means by the electrical discharge means for electrically attracting ions produced by the electrical discharge means away from the comminution means until comminuted material produced by the comminution means builds up sufficient space charge to divert the ions toward the charged comminuted material to enable the ions at least primarily to discharge the comminuted material.

2. A device according to claim 1, wherein the electrical discharge means are spaced from the comminution means in a direction transverse to a general direction.

3. A device according to claim 1, wherein the electrical discharge means surround or are provided on either side of the comminution means.

4. A device according to claim 1, wherein the ion attracting means surround or are provided on either side of the electrical discharge means.

5. A device according to claim 1 claims, wherein the ion attracting means comprises an electrically conductive or semiconductive perforate wall.

6. A device according to claim 1 claims, wherein the ion attracting means comprises an electrically conductive or semiconductive coating provided on an inner surface of a housing of the device.

7. A device according to claim 1, wherein in a general direction of production of comminuted material from the comminution means, the electrical discharge means is located at about a same position as the comminution means.

8. A device according to claim 1, wherein the electrical discharge means comprises a plurality of electrical discharge sites symmetrically located with respect to the comminution means.

9. A device according to claim 1, wherein the comminution means comprises a plurality of comminution sites.

10. A device according to claim 1, wherein an arrangement of the comminution means, the electrical discharge means and the ion attracting means is rotationally symmetric with the electrical discharge means and the ion attracting means being located on respective circles concentric with the comminution means.

11. A device according to claim 1, wherein the comminution means comprises an array of comminution sites and the electrical discharge means and ion attracting means each comprise a pair of elongate electrodes or arrays of electrodes disposed on either side of the array of comminution sites.

12. A device according to claim 1, wherein the liquid supply means comprises a liquid reservoir and a pump for supplying liquid from the liquid reservoir to the comminution means.

13. A device according to claim 12, wherein the pump comprises a pump selected from the following types: a diaphragm pump; an electroosmotic pump; and an electrohydrodynamic pump.

14. A device according to claim 12, wherein the pump comprises a flexible diaphragm arranged to flex in response to application of a control signal to diaphragm control means.

15. A device according to claim 14, further comprising valve means for controlling supply of liquid from the liquid reservoir to the pump.

16. A device according to claim 14, wherein the diaphragm control means comprises a piezoelectric element.

17. A device according to claim 12, wherein the pump comprises a syringe body and a syringe piston and user-operable means operable by a user are provided for moving the piston to cause a dose at liquid to be dispenses to the comminution means.

18. A device according to claim 17, wherein the user-operable means comprises a spring biassing mechanism.

19. A device according to claim 17, comprising means for controlling the amount of movement of the piston to control the amount of liquid supplied to the comminution means.

20. A device according to claim 12, wherein the pump comprises means for applying pressure to a moveable/collapsible or deformable portion of a liquid reservoir to shrink the liquid reservoir.

21. A device according to claim 20, wherein the pressure applying means comprises a spring or a gas pressure system.

22. A device according to claim 1, further comprising controlling means for controlling the amount of liquid supplied to the comminution means.

23. A device according to claim 22, wherein the controlling means are adjustable to enable the amount of liquid supplied to the comminution means to be manually adjustable.

24. A device according to claim 1, wherein valve means are provided for controlling a liquid outlet to the comminution means.

25. A device according to claim 24, wherein the comminution means comprises a rod having at least an electrically conductive end, the rod extending through an electrically insulative liquid supply tube and cooperating with an outlet of the liquid supply tube to form the valve means, means being provided for moving the rod relative to the tube to open the valve means to enable supply of liquid for communition.

26. A device according to claim 1, further comprising valve means for closing the liquid supply means to inhibit evaporation of liquid when the comminution means is not in use.

27. A device according to any one of claims 1 to 24 or 26, wherein the ion attracting means is arranged to be at a potential intermediate that of the comminution means and the electrical discharge means in use.

28. A device according to any one of claims 1 to 24 or 26, wherein the comminution means is coupled to a first reference potential source, the ion attracting means is coupled to the first reference potential source via a resistance and the electrical discharge means is coupled to a second, different, reference potential source.

29. A device according to claim 28, wherein the second reference potential is negative with respect to the first reference potential.

30. A device according to claim 1, comprising control means for causing liquid to be supplied to the comminution means prior to actuation of the comminution means.

31. An inhaler comprising a device in accordance with claim 1 and means for delivering at least partially electrically discharged comminuted material to the respiratory system of an animal.

32. A dispensing device comprising:

a housing having an outlet for supplying comminuted material, the housing containing:

a comminution means of subjecting liquid to an electric field for causing comminution of the liquid to produce cloud of charged comminuted material in a comminution chamber within the housing;

means for supplying liquid to the comminution means;

electrical discharge means at least partially surrounding the comminution means for producing ions to at least partially electrically discharge comminuted material produced by the comminution means;

ion attracting means spaced from the comminution means by the electrical discharge means away from the comminution means until comminuted material produced by the comminution means builds up sufficient space charge to divert the ions towards the cloud of charged comminuted material to enable the ions to at least partially discharge the comminuted material;

means for allowing air to enter the comminution chamber; and voltage supply means for supplying electrical discharge means and ion attracting means.

33. A device according to claim 32, wherein the ion attracting means comprises an electrically conductive or semiconductive inner wall spaced from an inner surface of the housing which wall is perforate and together with at least one air inlet provided in the housing provides the means for allowing air to enter the comminution chamber for reducing impact of comminuted material on the electrically conductive or semiconductive inner wall.

34. A method of delivering a medicament to the respiratory system of an animal which comprises using a device in accordance with any one of claims 1 to 30 to deliver comminuted material to the respiratory system of the animal.

35. A dispensing device comprising a device in accordance with any one of claims 1 to 31 or an inhaler in accordance with the claim 31 having a supply of an olfactory system affecting substance such as an olfactory represent or an olfactory stimulant such as aroma perfume.

36. A dispensing device in accordance with any one of claims 1 to 31 adapted for the delivery of insect repellent, insect attractant, a biocide, an insecticide, pesticide or other airborne product.

37. A dispensing device, comprising:

a comminution apparatus arranged and configured to subject liquid to an electric field that results in comminution of the liquid to produce charged comminuted material;

a supplier of liquid to the comminution apparatus;

an electrical discharger that is arranged and configured to produce ions to at least partially electrically discharge comminuted material produced by the comminution apparatus;

an ion attracter that is configured and arranged to electrically attract the ions away from the comminution apparatus until the comminuted material builds up sufficient space charge to divert the ions at least partially to discharge the comminuted material;

wherein said electrical discharger substantially surrounds said comminution apparatus and is interposed between the comminution apparatus and the ion attracter.

38. A dispensing device, comprising:

a housing having an outlet configured and arranged to supply comminuted material, the housing containing:

a comminution apparatus arranged and configured to subject liquid to an electric field to result in comminution of the liquid to produce a cloud of charged comminuted material in a comminution chamber within the housing;

a supplier of liquid to the comminution means;

an electrical discharger at least partially surrounding the comminution apparatus to produce ions to at least partially electrically discharge the comminuted material produced by the comminution apparatus;

an ion attracter that is spaced from the comminution apparatus by the electrical discharge means and the bounds the comminution chamber to electrically attract the ions away from the comminution apparatus until the comminuted material product by the comminution apparatus builds up sufficient space change to divert the ions towards the cloud of charged comminuted material to enable the ions to at least partially discharge the comminuted material;

a conduit that is arranged to allow air to enter the communication chamber, and a voltage supply arranged and configured to supply electrical potentials to the comminution apparatus, the electrical discharger and the ion attracter.

39. A dispensing device comprising:

a liquid supplier having a liquid outlet;

a discharge electrode spaced from the liquid outlet in a direction perpendicular to the direction of flow of liquid to the liquid outlet;

a further electrode spaced apart from the liquid outlet and the discharge electrode in said direction; and a voltage supplying arrangement configured to couple the further electrode to a first voltage, to couple the liquid outlet to a second voltage and to couple the discharge electrode to a third voltage wherein the first voltage lies between the second and third voltages and the second voltage causes comminution of liquid issuing from the liquid outlet.

40. A device according to claim 39, wherein the first voltage is ground.

41. A device according to claim 39, wherein the second voltage is negative with respect to the first voltage and the third voltage is positive with respect to the first voltage.

42. A device according to claim 39, wherein the first voltage is ground, the second voltage is negative with respect to the first voltage and the third voltage is positive with respect to the first voltage.

43. A device according to claim 39, wherein the second voltage is positive with respect to the first voltage and the third voltage is negative with respect to the first voltage.

44. A device according to claim 37, wherein the first voltage is ground, the second voltage is positive with respective to the first voltage and the third voltage is negative with respect to the first voltage.

45. A dispensing device comprising:

a liquid supply tube having an axis and a liquid outlet;

a discharge electrode spaced from the liquid outlet in a direction perpendicular to the axis;

a further electrode spaced apart from the liquid outlet and the discharge electrode in said direction; and a voltage supplying arrangement configured to couple the further electrode to a first voltage, to couple the liquid outlet to a second voltage and to couple the discharge electrode to a third voltage wherein the first voltage lies between the second and third voltages and the second voltage causes comminution of liquid issuing from the liquid outlet.

46. An inhaler according to claim 45, wherein the discharge electrode extends parallel to the further electrode and liquid supply tube.

47. A device according to claim 45, wherein the discharge electrode is engaged toward the liquid outlet.

48. A device according to claim 45, wherein the further electrode comprises a cage surrounding the liquid outlet.

49. A device according to claim 45, wherein an end of the further electrode, an end of the discharge electrode and the liquid outlet lie substantially on a line.

50. A device according to claim 45, wherein the further electrode extends beyond a line connecting the liquid outlet and the discharge electrode.

51. A dispensing device comprising:

an elongate liquid supply tube extending in a first direction and having a liquid outlet;

a discharge electrode spaced from the liquid outlet in a second direction perpendicular to the first direction;

a further electrode spaced apart from a comminution site in said second direction and extending substantially parallel to the elongate liquid supply tube; and a voltage supplying arrangement configured to subject the further electrode to a first voltage, the liquid outlet to a second voltage and the discharge electrode to a third voltage wherein the first voltage lies between the second and third voltages and the second voltage causes comminution of liquid issuing from the liquid outlet.

52. A dispensing device comprising:

a liquid supply tube having an axis and a liquid outlet;

a discharge electrode spaced from the liquid outlet in a direction perpendicular to the axis and angled towards the liquid outlet;

a further electrode separate from the discharge electrode and spaced apart from the liquid outlet in said direction; and a voltage supplying arrangement configured to couple the further electrode to a first voltage, to couple the liquid outlet to a second voltage and to couple the discharge electrode to a third voltage wherein the first voltage lies between the second and third voltages and the second voltage causes comminution of liquid issuing from the liquid outlet.

53. An inhaler for dispensing a medicament to a user, the inhaler comprising:

a housing;

a liquid reservoir within the housing;

a liquid supply pipe configured to supply liquid from the reservoir to a comminution site;

a discharge electrode spaced from the comminution site;

a further electrode spaced from the comminution site;

a voltage supplying arrangement configured to subject the further electrode to a first voltage, the liquid outlet to a second voltage and the discharge electrode to a third voltage wherein the first voltage lies between the second and third voltages and the second voltage causes comminution of liquid issuing from the liquid outlet to produce comminuted matter;

wherein the housing has an outlet for supplying comminuted matter to a user upon inhalation by the user and wherein the housing, comminution site, discharge electrode and further electrode are configured such that the comminution site, discharge electrode and further electrode are spaced apart in a direction perpendicular to a general direction of flow of comminuted matter to the outlet.

54. An inhaler according to claim 53, wherein the discharge electrode extends parallel to the further electrode and liquid supply pipe.

55. An inhaler according to claim 53, wherein the discharge electrode is angled toward the comminution site.

56. An inhaler according to claim 53, wherein the further electrode comprises a cage surrounding the comminution site.

57. An inhaler according to claim 53, wherein an end of the further electrode, an end of the discharge electrode and the comminution site lie substantially on a line.

58. An inhaler according to claim 53, wherein the further electrode extends beyond a line connecting the comminution site and the discharge electrode.

* * * * *

UNITED STATES PATENT AND TRADEMARK OFFICE

CERTIFICATE OF CORRECTION

PATENT NO. : 6,595,208 B1

DATED : July 22, 2003
INVENTOR(S) : Coffee, R. and Pirri, A.

It is certified that error appears in the above-identified patent and that said Letters Patent is hereby corrected as shown below:

Column 15,
Line 67, should read as follows:
-- … to a general direction in which comminuted material is supplied from the comminution means. --

Signed and Sealed this

Eighth Day of June, 2004

JON W. DUDAS
*Acting Director of the United States Patent and Trademark Office*